(12) United States Patent
Rump (10) Patent No.: US 6,566,894 B2
(45) Date of Patent: *May 20, 2003

(54) PROCESS AND DEVICE FOR DETECTING OXIDIZABLE AND/OR REDUCIBLE GASES IN AIR

(75) Inventor: Hanns Rump, Wohnsitz (DE)

(73) Assignee: Rosemarie Brand-Gerhart, Hausen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 27 days.

(21) Appl. No.: 09/183,376

(22) Filed: Oct. 30, 1998

(65) Prior Publication Data

US 2002/0011851 A1 Jan. 31, 2002

Related U.S. Application Data

(63) Continuation-in-part of application No. PCT/EP97/02208, filed on Apr. 29, 1997.

(30) Foreign Application Priority Data

Apr. 30, 1996 (DE) .......................................... 196 17 297

(51) Int. Cl.[7] .......................... G01R 27/26; G01N 27/30; G01N 27/60

(52) U.S. Cl. ..................... 324/681; 324/658; 204/432; 436/151

(58) Field of Search ............................. 324/464, 470, 324/486, 663, 667, 610, 674, 681, 693, 703, 707, 71.7; 204/432; 422/90, 94, 98; 436/149, 151, 152

(56) References Cited

U.S. PATENT DOCUMENTS

| 4,146,834 A | * | 3/1979 | Maltby et al. ............... 324/610 |
| 4,755,473 A | * | 7/1988 | Nishino et al. ............. 436/133 |
| 4,770,761 A | | 9/1988 | Burggraaf et al. .......... 204/425 |
| 4,864,462 A | * | 9/1989 | Madou et al. ............... 361/280 |
| 4,906,440 A | | 3/1990 | Kolesar, Jr. ................... 422/98 |
| 5,019,517 A | * | 5/1991 | Coulson ..................... 436/153 |
| 5,387,462 A | | 2/1995 | Debe .......................... 428/245 |
| 5,965,451 A | * | 10/1999 | Plog et al. ................... 436/139 |

FOREIGN PATENT DOCUMENTS

| DE | 3827426 | 2/1990 |
| DE | 3917853 | 12/1990 |

OTHER PUBLICATIONS

J. Gutierrez "Sensors and actuators", vol. 4, 1991 pp. 359 to 363.

* cited by examiner

Primary Examiner—N. Le
Assistant Examiner—Anjan K. Deb
(74) Attorney, Agent, or Firm—Horst M. Kasper (57) ABSTRACT

A device and method for detecting oxidizable and/or reducible gases in the air for controlling ventilation plants in buildings or motor vehicles and for monitoring combustion processes or waste gas analysis by a capacitance sensor that detects change in sensor capacities at two different frequencies. Alternating currents having at least two frequencies is passed through a heated sensor between contact electrodes of the sensor and a polycrystalline metal oxide sensor material and an evaluation circuit measures a change in capacitance between the electrodes and sensor material. A change in capacitance measured at a first frequency indicates the presence of reducible gases while a change in sensor capacitance at a second frequency indicates the presence of oxidizable gases. Variations in sensor ohmic resistance at the two frequencies are also considered.

24 Claims, 7 Drawing Sheets

PROCESS AND DEVICE FOR DETECTING OXIDIZABLE AND/OR REDUCIBLE GASES IN AIR

CROSS REFERENCE TO RELATED APPLICATIONS

This application is a continuation-in-part application of another international application filed under the Patent Cooperation Treaty on Apr. 29, 1997, bearing Application No. PCT/EP97/02208, and listing the Untied States as a designated and/or elected country. The entire disclosure of this latter application, including the drawings thereof, is hereby incorporated in this application as if fully set forth herein.

BACKGROUND OF THE INVENTION

1. Field of the Invention

The invention relates to a method for detection of oxidizable and/or reducible gases in the air for the purpose of controlling devices for ventilation in buildings or vehicles and for the purpose of surveillance of combustion processes or of waste gas catalyst plants, by employing at least one heated and current-passing sensor, furnished with contact electrodes and made of a metallic sensor material, as well as by employing an electrical evaluation circuit, wherein the sensor is passed through by an alternating current, which alternating current either comprises at least two alternating currents of different frequencies or is switched between at least two frequencies, and wherein, on the one hand, the change of the capacitances between the sensor material and the contact electrodes is evaluated by the evaluation circuit as an indicator of a presence of reduceable gases and, on the other hand, the change of the capacitances within the mass of the sensor material (sensitive material) is evaluated as an indicator of the presence of oxidizable gases, as well as to a device for the performance of the method.

2. Brief Description of the Background of the Invention Including Prior Art

It is necessary in numerous cases to have knowledge about the kind and concentration of gases present in the breathable air in order to be able to perform technical control processes and technical automatic control processes or in order to be able to perform steps for the protection of the human being relative to dangerous or unpleasant, smelling gases. The knowledge of the contents of damaging materials inside or outside of the living space of the human being is important in particular for the purpose of the necessary and situation-required ventilation, in order to either initiate the ventilation or in order to interrupt the feeding of outside air when concentrations of damaging gas are present outside of the region to be ventilated.

During the surveillance or automatic control of combustion processes it is important to know the concentration of non-combusted hydrocarbons or of carbon monoxide or, respectively, the concentration of nitrous oxides in the waste gas. It is necessary in the course of monitoring the function of catalysts, for example, in motor vehicles, to know the concentration of gases before and after the catalyst, in order to be able to determine the degree of effectiveness of the catalyst.

It is a property of all examples that both, oxidizable gases, hydrocarbons, carbon monoxide, etc., as well as of reducible gases, in particular nitrous oxides, are to be detected for a determination of the individual situation and for the control of processes or, respectively, for the initiation of proper steps.

Based on the massive requirement of such sensors, technologies are sought which are not associated with large financial costs. Sensors based on polycrystalline metal oxides are associated with favorable costs and are sturdy and have been proven in practical situations. However, at this time experiences exist in fact relative to the detection of oxidizable materials, but hardly any experiences or practical solutions exist relative to the detection of both oxidizable gases as well as reducible gases, which occur simultaneously and which are to be detected at the same time, i.e. simultaneously, without making the costs and the equipment requirements too expensive relative to the application.

In principle, metal oxide sensors change their electrical resistance upon presence of a gas. The generally known sensors consist of a heated and contacted layer made for example of tin dioxide or of another metal oxide such as, for example, zinc oxide, gallium oxide, tungsten trioxide, aluminum vanadate, and other sensitive materials, wherein the sensor material is applied in a thin film technique or a thick film technique to a substrate made of ceramics or silicon and exhibits contact electrodes. If an oxidizable gaseous material impinges onto the sensor, then the metal oxide releases oxygen and becomes therefore reduced, whereby the conductivity value is increased. This process is reversible because the heated metal oxide combines later again with the oxygen of the air. The conductivity value of the sensor material is a function of the concentration of the oxidizable gases present, since a continuous exchange process is present between the offered gas, the metal oxide and the oxygen of the air and because the concentration of the oxygen of the air is a quasi constant value.

The electrical effect is opposite in case of reducible gases such as ozone, nitrous oxides and the like, because the sensitive material of the sensor is in no case a pure metal oxide, but instead this metal oxide is always in part reduced [$SnO (2-x)$]. Thus, the conductivity value is therefore lowered in case of an application of gas to the sensor. Complex chemical reactions between the gases with the sensor material as well as of the gases amongst each other occur in the simultaneous presence of oxidizable gases and of reducible gases in the neighborhood of the hot surface of the sensor, furnished with catalytic materials such as for example platinum or palladium. An unequivocal statement relating to the concentration of the gases present cannot be made up to now in this case.

It has been observed that the reactivity of metal oxide sensors relative to oxidizable or reducible gases is dependent on temperature. In case of low temperatures of for example below 150° C., the tin dioxide sensors are only slightly sensitive relative to oxidizable gases and hardly at all react with a conductivity-value increase upon application of a gas. If however reducible gases are present, the sensor reacts immediately with a significant decrease in the value of the electrical conductivity. For this reason it has been proposed to switch either sensor groups of in each case constant temperature based on the different reactions of the sensor in case of high (above 300° C.) temperatures and of low (below 150° C.) temperatures, which sensor group is in each case more sensitive for the group of gases involved.

It is known from the German printed patent document DE-A-38 27 426 to vary the temperature of the sensor and thus to obtain the desired information with a single sensor. This method has not proven to be of practical interest, because it takes a long time for the sensor to recover a standard value after applying the gas to the sensor at a low temperature. It has further being observed that the metal oxide sensors have under no circumstances an Ohmic resistance changeable depending on the gas present, as is frequently reported in a simplified fashion.

A method is known from the German printed patent document DE-A-3917853, where the impedance course of the sensor element is determined through the frequency of an alternating current and is employed for the identification of the gas present. J. Gutierrez describes the electrical equivalent circuit diagram of a tin dioxide sensor (FIG. 1) as a combination of resistors and capacitors and determines that all parameters are changed upon presence of a gas, in the literature citation "Sensors and Actuators, Volume 4, 1991, pp. 359 to 363".

An electrically reactive compound device has in addition become known from the U.S. Pat. No. 5,387,462, which compound device exhibits random and regular fields of microstructures, which are in part disposed within an enveloping layer, wherein each microstructure exhibits a structure similar to a hair crystal and possibly exhibits a cover layer, wherein the cover layer envelopes the hair-crystal-like structure. The compound device is electrically conducting and serves as a component of an electrical switching circuit, of an antenna, of a micro-electrode, as a reactive heating element, or as a multimode sensor, in order tQ prove a presence of vapors, gases or liquids. The change of the orientation of the hair-like crystals is employed for measuring a presence of the material to be detected.

Technical Object:

It is object of the present invention to furnish a method and an apparatus which is or, respectively, are capable to detect simultaneously both groups of gases, namely oxidizable gases as well as reducible gases with one and the same sensor based on metal sensors, such as in particular the known metal oxide sensors.

SUMMARY OF THE INVENTION

1. Purposes of the Invention

It is a purpose of the invention to furnish a separate statement relative to the change of the electrical path resistance and to the change of the electrical contact resistance such that as statement relative to the presence and to the concentration of oxidizable gases and/or reducible gases can be made based on a single sensor.

These and other objects and advantages of the present invention will be come evident from the description which follows.

2. Brief Description of the Invention

The solution of the object resides with respect to a method in that the sensor is passed through by an alternating current, which alternating current consist either out of at least two alternating currents of different frequency is or which alternating current is switched between at least two frequencies, wherein on the one hand the change of the capacities between the sensor material and the contact electrodes is evaluated as being typical for the presence of reducible gases and on the other hand the change of the capacitances within the mass of the sensor material (sensitive material) is evaluated as typical for the presence of oxidizable gases, and wherein the changes of the Ohmic resistance components of the sensor material are considered in connection with the changes depending on the gas.

The sensor can be a component of an oscillator circuit for the generation of two different frequencies, wherein the oscillation of the oscillator circuit is periodically changed by switching the frequency-determining components between at least two frequencies, wherein the respective frequencies are individually evaluated and are compared to the respective frequencies determined during operation of the sensor in standard air and frequency deviations are employed as a measure for the concentration of present gas groups, wherein high frequencies are always coordinated to reducible gases and wherein low frequencies are always coordinated to oxidizable gases. According to a further embodiment, the phase shifts caused by the sensor-internal capacities are determined at the individual frequencies, and the output signal is decomposed into an imaginary part and into a real part, which imaginary part and real part represent a measure for the presence and for the kind of gases relative to the values determined under standard air conditions. Furthermore, the temperature of the sensor can be switched simultaneously with the switching of the frequencies, wherein the lower frequency is coordinated to the higher temperature and wherein the higher frequency is coordinated to the lower temperature.

A device is characterized in that the sensor is passed through by alternating current, which alternating current consists of at least two alternating currents of different frequencies or which is switchable between at least two frequencies, wherein on the one hand the change of the capacities between the sensor material and the contact electrodes is evaluated as typical for the presence of reducible gases and on the other hand the change of the capacities within the mass of the sensor material (sensitive material) is evaluated as typical for the presence of oxidizable gases, and wherein the gas-dependent changes of the Ohmic resistance components of the sensor material are considered in context.

The advantage of the method and of the device for this purpose comprise that both gas groups, namely oxidizable gases as well as reducible gases can be detected simultaneously with one and the same sensor, such as a metal sensor, in particular the conventional metal oxide sensors, wherein the device can be produced under favorable cost conditions.

The invention is based on the observation that the reaction mechanisms of oxidizable gases or of reducible gases, which are capable of being electrically evaluated, are substantially different. In case of an offer of oxidizable gases, for example of carbon monoxide CO, the Ohmic conductivity value of the mass of the sensor material changes as such by the reduction of the material. Also, the transition capacitance at the crystal transitions (path resistance) within the material are changed in a significant way. In contrast, the transition capacitance at the contacts is changed hardly at all.

The sensor reacts differently when reducible gases, for example nitrogen oxide NO or nitrogen dioxide $NO_2$ are absorbed at the surface of the sensor material. Based on the lower reactivity, a lower change of the electrical parameters of the sensor mass (path resistance) or, respectively, of the sensor material occurs than in the case of oxidizable gases. However, a substantial influencing of the Schottky transitions occurs caused by the gas-induced boundary face states.

If therefore a sensor is operated only with direct current as a gas-dependent resistor, then the switching capacitances at the Schottky transitions become part of the background. Practically only the mass resistance of the polycrystalline metal oxide is evaluated.

One obtains in contrast other and substantially richer results, if the impedance of the sensor is considered within the framework of evaluation strategies. The invention furnishes therefore a device which allows the simultaneous detection both of oxidizable substances and of reducible substances with one single sensor, wherein the changes of the above described capacitances are employed and exploited, which changes are a function of the nature of the gas.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention.

DESCRIPTION OF THE INVENTION AND PREFERRED EMBODIMENTS

Figure 1:
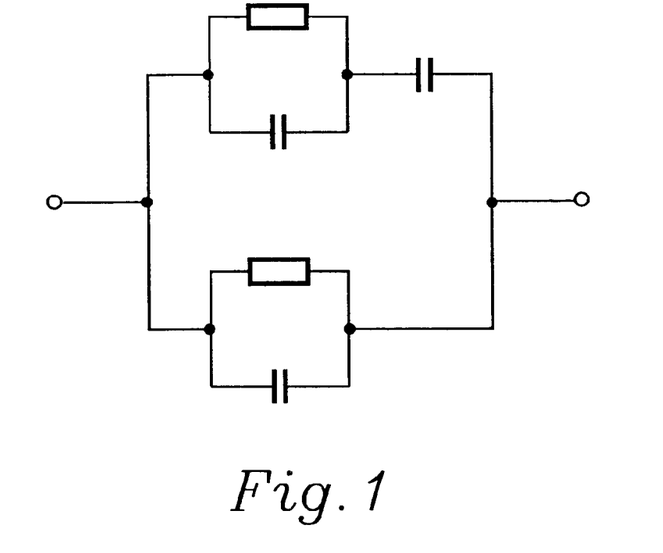
FIG. 1 shows an electrical equivalent circuit diagram of a sensor with tin dioxide as a sensor material as a combination of resistors and capacitors.

The electrical resistance of a metal oxide sensor is obtained on the one hand from the mass of the sensitive metal oxide and its Ohmic resistance or, respectively, the specific resistance. Schottky transitions with contact capacitances are already present between the individual crystals of the actual polycrystalline metal oxide as a function of the grain size and the thickness of the material, wherein the contact capacitances are switched sequentially and parallel. Transitions are obtained upon transition to the contact electrodes, which transitions are to be understood also as Schottky transitions with corresponding switching capacitances which is illustrated in FIG. 1 by way of a equivalent circuit diagram.

According to the present invention, a preferred sensor is made of a mixed oxide including tin dioxide ($SnO_2$) plus tungsten trioxide ($WO_3$) plus zinc oxide (ZnO) plus iron trioxide ($Fe_2O_3$). Preferably, these components are employed with the following weight percentages:

Tin dioxide from about 40 to 50 weight percent
Tungsten trioxide from about 35 to 45 weight percent
Zinc oxide from about 10 to 20 weight percent
Iron trioxide from about 2 to 10 weight percent A preferred composition contains 45 weight percent tin dioxide, 40 weight percent tungsten trioxide, 15 weight percent zinc oxide, and 5 weight percent iron trioxide.

The heatable sensor is preferably heated to temperatures from about 200 to 400° C. and more preferably to temperatures from about 300 to 350° C. and a practical value for such temperature can be 330° C.

The temperature regions of the lower temperature and of the higher temperature of the sensor during switching of frequencies can be from about ±10 to 100° C. and is preferably from about ±30 to 50° C. with a practical value of ±30° C. difference employed in practical examples.

A sensor can be obtained commercially from the company FIGARO Inc., Osaka, Japan, which sensor carries the type designation TGS 812.

Figure 2:
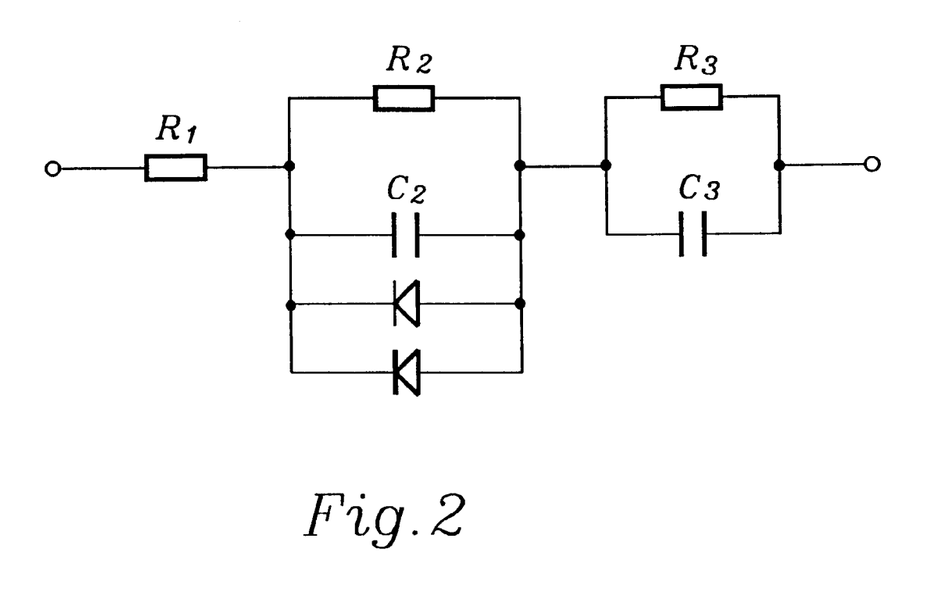
FIG. 2 shows an expanded, more precise electrical equivalent circuit diagram according to FIG. 1 based on the addition of contact capacitances and resistances of the contact electrodes.

FIG. 2 illustrates a more precise equivalent circuit diagram of the model according to FIG. 1, wherein R1 represents the volume part of the resistance, R2 represents the transition resistance of the metal oxide to the contacts, and C2 represents the capacitance at the Schottky transitions; resistor R3 and capacitor C3 describe the gas-dependent diffusion and migration effects of the sensitive material at the electrical transitions within the polycrystalline material of the sensor.

The capacitances at the contact transitions can be determined to be 10 to 100 pF, while the capacitances at the Schottky transitions of the grain boundaries within the material can assume values of 0.1 to 2 $\mu F$ depending on the grain size and the layer thickness.

Figure 3:
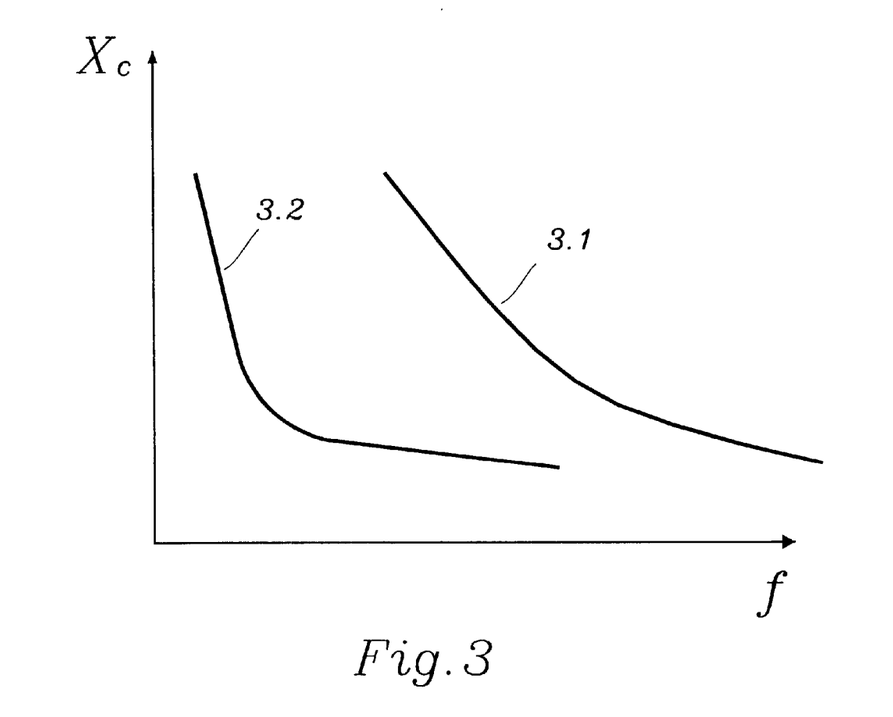
FIG. 3 shows two courses of the impedance, namely curve 3.2 showing the course of the impedance of the contact transition, and curve 3.1 showing the course of the impedance within the polycrystalline structure of the path resistance with larger capacities.
Figure 4:
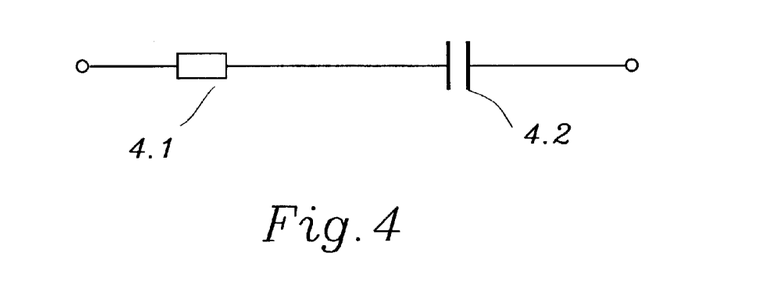
FIG. 4 shows the simplified equivalent circuit diagram of the sensor consisting only of a capacitor and of a resistor.

If according to FIG. 4 the equivalent circuit diagram of the sensor is roughly simplified as consisting of a series circuit of a single capacitor 4.2 and of a single resistor 4.1 in each case for the contact transition or, respectively, for the polycrystalline mass, there result impedance courses (capacity plotted versus the frequency) such as they are shown in FIG. 3. The course of the curve 3.2 is in this case the course of the impedance of the contact transition, the capacitances of which are substantially smaller and the capacitances of which take care of an impedance decreasing with the frequency up to a relatively high frequency. The Ohmic part of the series-connected path resistance prevails at very high frequencies such that the curve assumes an asymptotic course.

The substantially higher capacitances within the polycrystalline structure of the path resistance of the sensor material are responsible for that the curve 3.1 becomes asymptotic already at relatively low frequencies.

Of course, the two curves 3.1 and 3.2 cannot be represented ideally and separately as illustrated in FIG. 3 because the two effects occur simultaneously within the sensor. Rather, one will always determine an addition of the effects.

Figure 5:
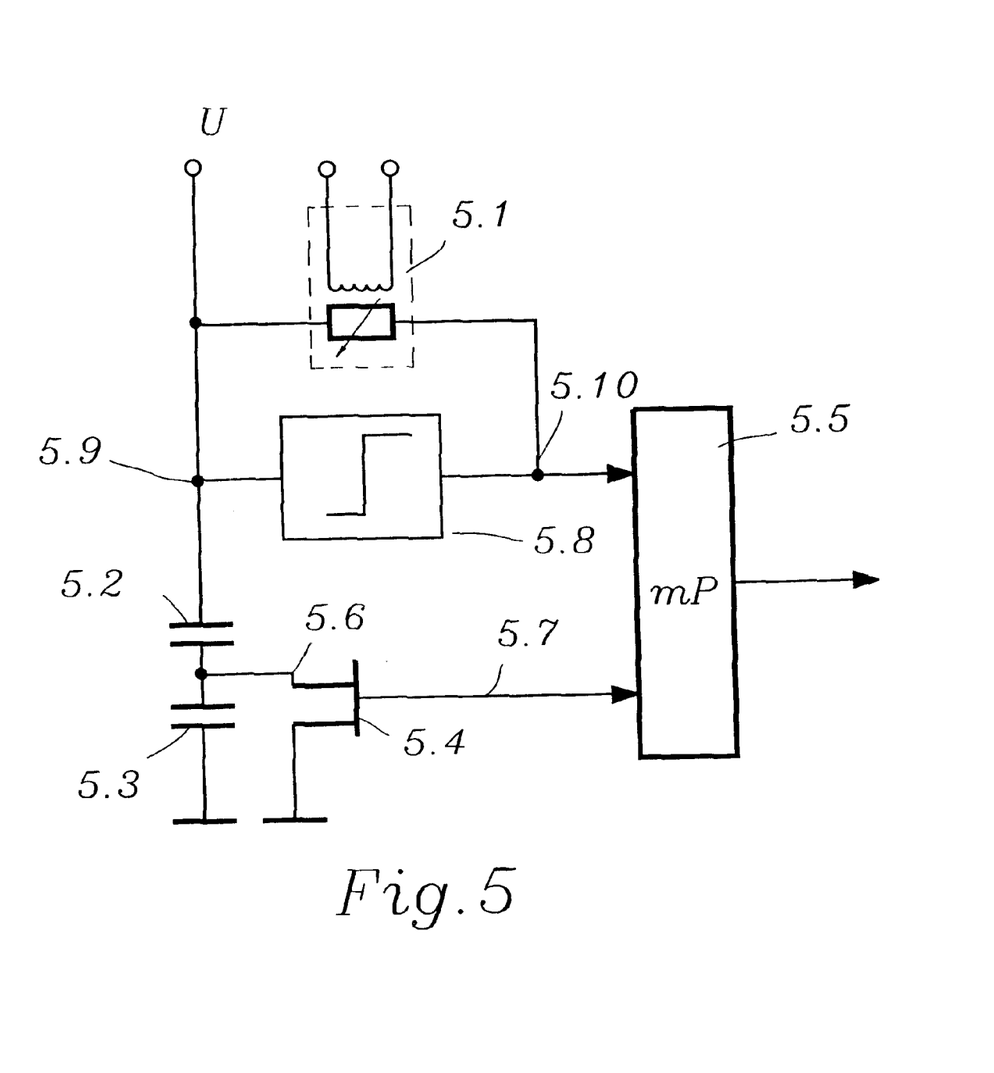
FIG. 5 shows a technical realization of a device with not too high a claim to the precision of the measurement.

In order to be able to exploit the described effects for purposes of measurement technology, several methods are described according to the present invention. For this purpose, FIG. 5 shows a technical realization of the device with not too high a claim to the precision of the measurement, which has proven itself for many purposes and which is sufficient. A sensor 5.1, heated to a temperature of, for example, 350° C. is a component of an oscillator circuit 5.8, preferably, the sensor 5.1 with its contact electrodes 5.9 and 5.10 is disposed parallel to the oscillator circuit 5.8. The output signal of the oscillator circuit 5.8 at the output 5.10 is applied to a micro-processor 5.5 ($\mu P$). A capacitor 5.2 is connected in series to a capacitor 5.3 and connected with the one input 5.9 of the oscillator circuit 5.8 or, respectively, with the one contact electrode 5.9 of the sensor 5.1, wherein the capacitor 5.3 can be short-circuited alternatingly or, respectively, periodically.

In case the oscillating circuit includes components which are switched in or out for determining different frequencies, then the switching frequency can be from about 2 hz to 100 hz and is preferably from about 5 hz to 20 hz and can be for example 10 hz.

The alternating short-circuiting of the capacitor 5.3 can for example occur in a field-effect transistor 5.4, wherein for example in a p-channel barrier-layer field effect the drain or, respectively, the source connection 5.6 is disposed centered between the capacitors 5.2 and 5.3, which is connected to the mass; the gate connection 5.7 is connected to the microprocessor 5.5 ($\mu$P). The field effect transistor 5.4 is controlled by the microprocessor 5.5. The circuit is laid out such that a frequency of about 3 to 5 khz of the oscillator circuit 5.8 results upon a short circuit of the capacitor 5.3 when the sensor 5.1 is adapted to standard air, whereas in contrast a frequency of about 150 khz of the oscillator circuit 5.8 results when the capacitors 5.3 and 5.2 are connected in series. The internal counter of the microprocessor 5.5 determines also the frequency delivered by the oscillator circuit 5.8. The input capacitances of the oscillator circuit 5.8 is changed correspondingly by a continuous switching of the field effect transistor 5.4 between short circuit of the capacitor 5.3 and the series connection of the capacitors 5.3 and 5.2, whereby the output frequency of the oscillator circuit 5.8 is changed. Advantageously, the ratio of the respective operating times is a selected such that the number of oscillations, read into the counter of the microprocessor 5.5, approximately correspond to each other. Since the frequencies have a ratio of about 1:30, the control ratio of the field effect transistor will be selected to be about 30:1.

In case of an oxidizable gas, the change in capacitance in case of full saturation amounts to from about 10 to 30 percent and can assume a value Delta-C of 20 percent.

In case of a reduceable gas, the change in capacitance amounts to form about 30 to 70 percent and can assume a value of Delta-C of 50 percent.

Figure 6:
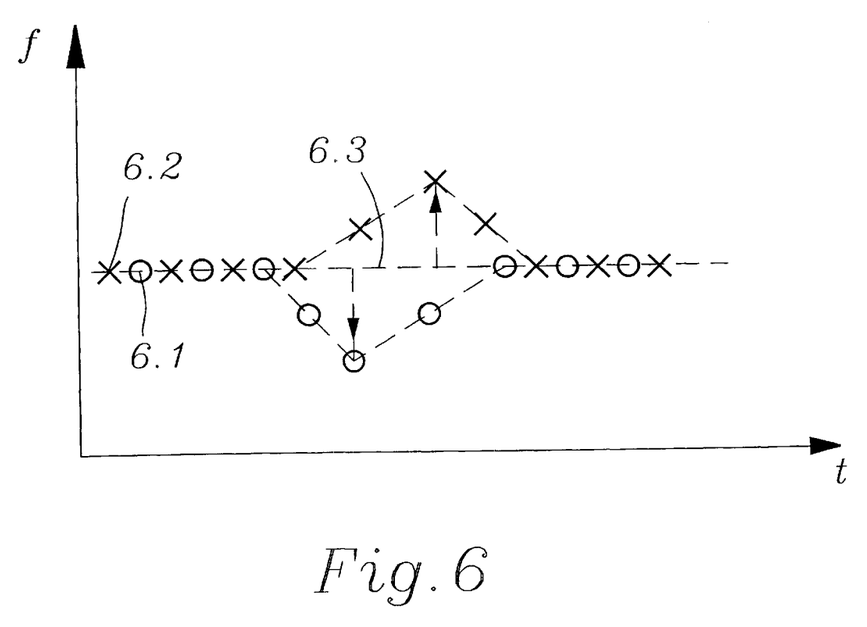
FIG. 6 shows the measurement results from the circuit according to FIG. 5 presented as a curve.

The micro-processor reads in each case the counter and coordinates the results in each case to a channel such that a picture is generated according to the picture shown FIG. 6. For this purpose, a curve 6.1 represents the results of the high frequency signals (o . . . ) and the other curve 6.2 represents the low frequency signals (x . . . ). The high frequency signals 6.1 are influenced to a substantially higher degree by the nitrogen oxides and other reducible gases as compared to the low frequency signals 6.2, which for practical purposes are only influenced by oxidizable gases. Since the reactions are counter running, the distance 6.3 of the signals (- . . . -) from each other is a measure for the sum of the gases present, which can be fully sufficient for example in regard to questions of the ventilation control of buildings or of motor vehicle cabins. The ventilation flap of a motor vehicle can be closed in cases where for example the distance 6.3 surpasses a defined size measure. Advantageously, a stationary signal is employed, which signal reliably detects for an unlimited time for example in tunnel situations an unusually high loading of the air.

Thus, the method according to be present invention is superior to known methods for the simultaneous detection of diesel waste gases and of gasoline waste gases because the known methods operate dynamically and do not generate any signals in case of a permanent level of the gas and for example would again open the ventilation flap in a tunnel extremely loaded with waste gases, which is not always desired. Of course, care has to be taken in programming technology that the data read in for standard air are employed for the calibration of the "zero line". In addition, the amounts of change are considered by a weight depending on the response sensitivity to the respective defined object gases, for which corresponding technologies are known, and these technologies are therefore not considered in the framework of the invention. In contrast, it is of highest interest in connection with the determination of combustion processes to know the respective parts of oxidizable gases and of nitrogen oxides. In this case, the deviation from the "zero line" characterizes the concentration of that respective gas, which can be evaluated by the microprocessor with a program installed for that purpose.

The method can be employed with the success also for on-board diagnoses (OBD) of motor vehicle catalysts, since the sensors are sturdy and economic and since the evaluation electronics also does not involve special requirements.

Of course, the presented switching circuit example is only one of a multitude of possibilities. The basic idea according to the invention, however, includes to switch the alternating current, employed for the evaluation, back and fourth between two frequencies and to evaluate the obtained data such that one information gives the sum of the gases present or, respectively, the concentration of the oxidizable gases present and of the reducible gases present, by capturing the specific changes at the respective frequencies in comparison to standard air with a suitable electronic evaluation circuit.

The two alternating currents of different frequencies within the sensor can be selected between 1 hz and 1 MHz, and are preferably between 100 hz and 10 khz. The frequency of the alternating current having a higher frequency can be from about 2 to 10,000 times the value of the frequency of the alternating current having a lower frequency and is preferably from about 10 to 1,000 times the frequency of the alternating current having a lower frequency.

Figure 7:
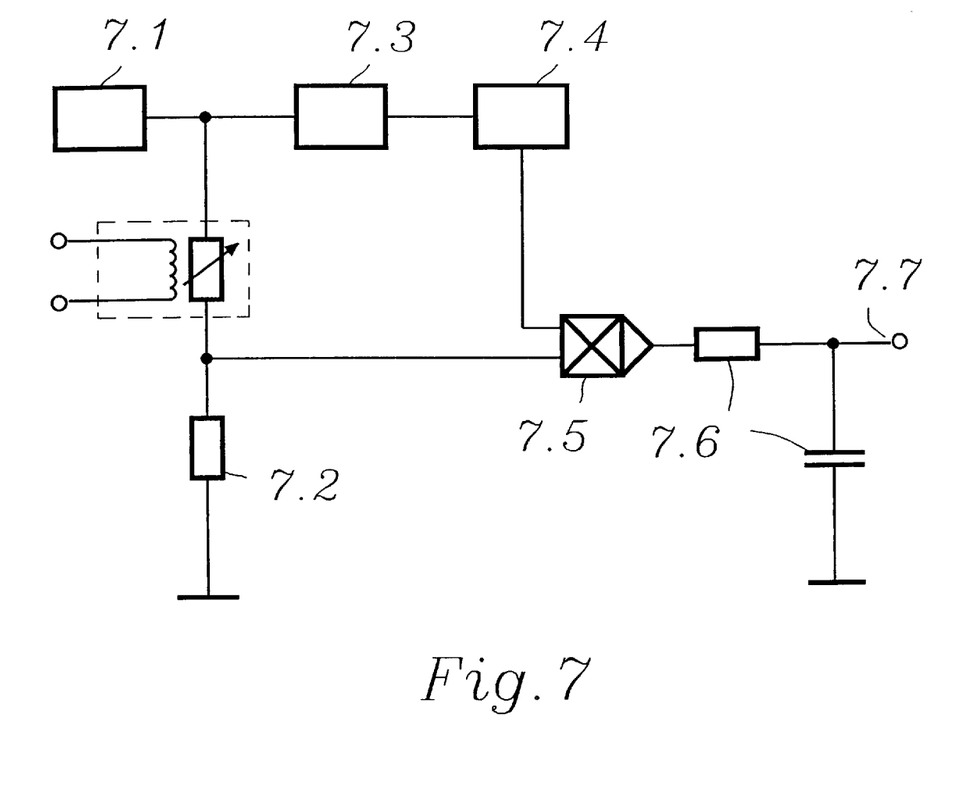
FIG. 7 shows a technical realization of a device with a high precision of the measurement.

In case of higher requirements in regard to measurement precision, the above recited base idea remains in fact intact to scan the frequency of the operating voltage of the sensor between the two recited frequencies. FIG. 7 shows a technical realization of a device with high measurement precision. For this purpose, according to a further embodiment of the invention method, the signal is decomposed into the real part and into the imaginary part in each case for each frequency by a phase consideration with the aid of a suitable comparison circuit according to the state of the art. The information obtained in this manner is more precise than the previously described method in connection with FIG. 5 but requires somewhat higher expenditures.

For this purpose, an alternating current from a generator 7.1 is fed to a sensor 7.2 through a phase shifter 7.3 and a rectangular wave modulator 7.4, which generator 7.1 is capable of generating alternating currents of different frequencies. The output signal of the rectangular wave modulator 7.4 and the voltage, tapped through the sensors 7.2, are fed to a mixer 7.5, for example a multiplier, wherein the output signal of the multiplier is averaged over a low pass 7.6. The output voltage 7.7, obtained after the low pass 7.6, represents, depending on, the setting of the phase shifter 7.3, a measure for the imaginary part and for the real part or for a mixture of the two components of the complex sensor resistor (compare the principle of the phase-proper rectifier pp.).

The thus enabled separation of the real part and of the imaginary part of the complex sensor resistor permits the distinction of capacitive and resistive effects at the sensor 7.2. This allows the distinction or, respectively, the simultaneous measurement of gases, which gases are distinguished by different reaction mechanisms at different places of the sensor, namely at the grain boundaries or at the metal semiconductor contact. In addition, several absorption effects and change charge effects with in part opposite results on the real part on the sensor resistor can occur upon the adsorption of gases on semiconductor sensors (HL-sensors), which renders a quick and reliable detection of the gas difficult.

Figure 8:
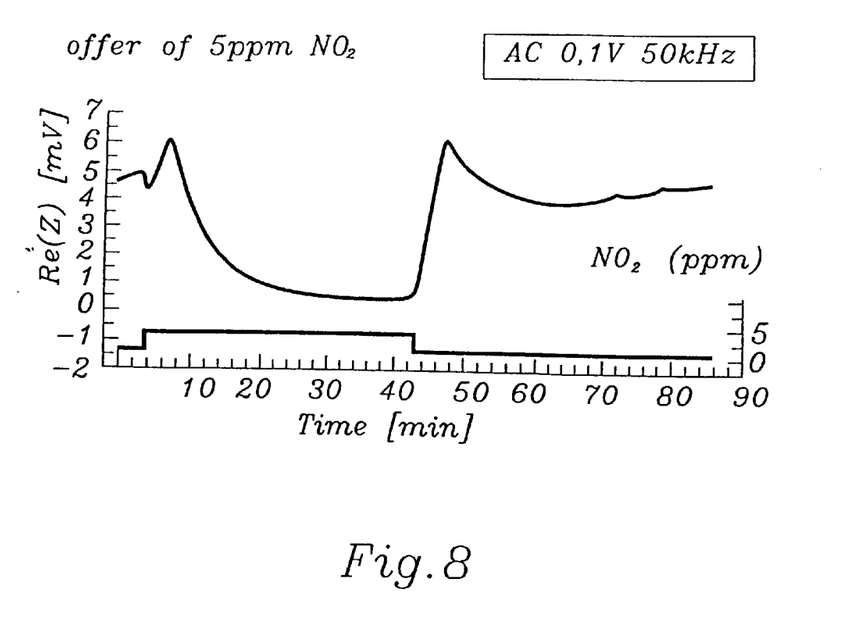
FIG. 8 shows a curve for the real part of the sensor resistance according to the device of FIG. 7 in the presence of five parts per million of nitric oxide $NO_2$ in synthetic air, plotted over the time axis.
Figure 9:
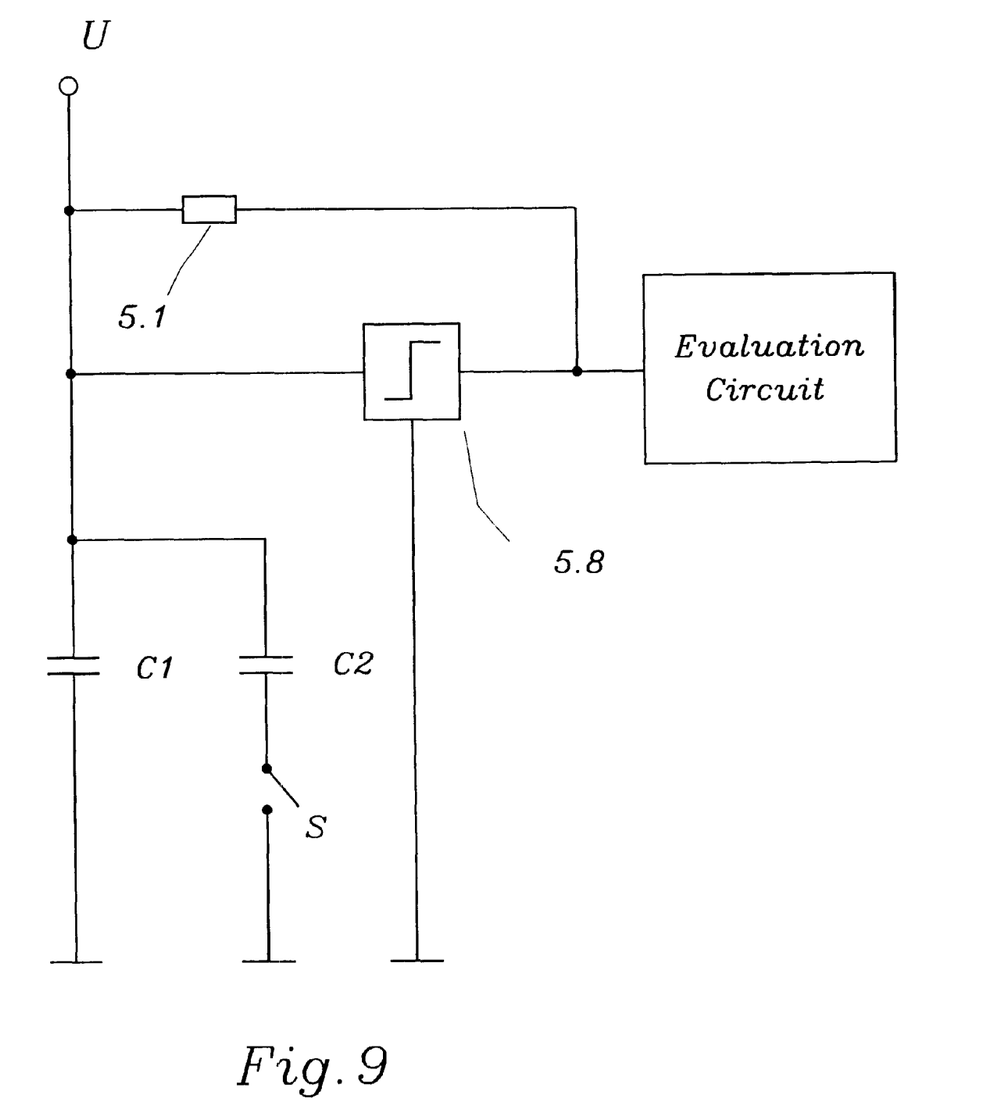
FIG. 9 shows a parallel connection of the two capacitors as a frequency determining cuircuit and which comprises a 'real' switching element.
Figure 10:
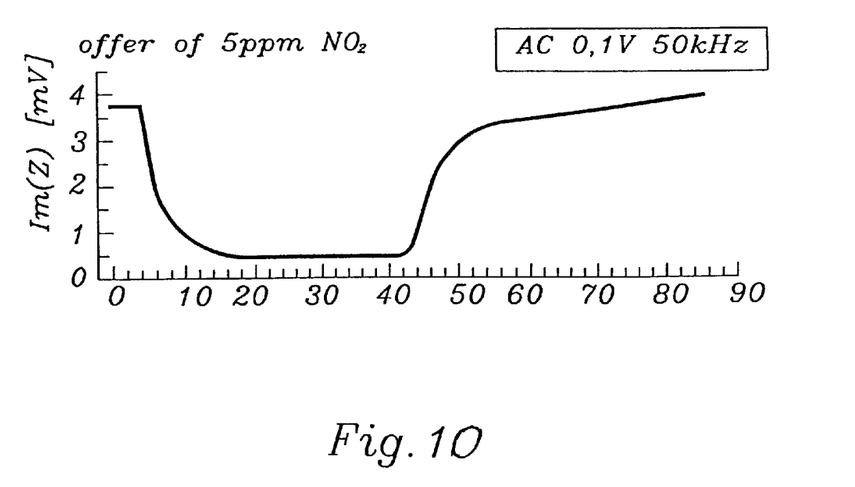
FIG. 10 shows a curve for the imaginary part of the sensor resistance according to the device of FIG. 7 in the presence of five parts per million of nitric oxide $NO_2$ in synthetic air, plotted over the time axis.

FIG. 8 and FIG. 10 show two curves for the real part and for the imaginary part of the sensor resistance according to the device of FIG. 7 in the presence of 5 ppm $NO_2$ in synthetic air, applied over a time axis. The employment of the imaginary part of the sensor resistor can lead in this case to a higher detection reliability and to a quicker detection. The imaginary part and the real part of the sensor resistance of a metal oxide sensor are plotted in FIG. 8 and FIG. 10 relative to the time in minutes in case of the presence of 5 ppm nitrogen dioxide $NO_2$ in synthetic air. The curves were plotted with an arrangement according to FIG. 7 with an applied sinus voltage of 0.1 volts and a frequency of 50 khz. While the real part of the sensor resistance shows two oppositely directed effects and could be used for a reliable evaluation only ten minutes after the start of the presence of the gas, the imaginary part of the sensor resistor shows from the beginning of the presence of the gas an unequivocal and evaluatable change in direction and reaches already after about 6.5 minutes 90 percent of its final change.

In addition to the previously described methods, it is proposed to modulate a lower frequency, for example of 1 khz, to a higher carrier frequency, for example of 250 khz, and to analyze the resulting signal according to be teaching previously stated. It is also possible to employ a mixture of the various frequencies with respect to changes of the phase position relative to each other in the sense of the precedingly stated teaching. Finally, it is conceivable to tune slidingly the frequencies and to analyze slidingly the signal in an imaginary part and/or in a real part and to plot them, or, respectively, to feed them for further processing.

It is apparent that the capability of providing information of a sensor arrangement can be substantially improved if the described method is employed with a presence of several simultaneous sensor elements. If the sensor elements employed are operated at different temperatures or are composed of different sensitive materials, then a multitude of information is furnished by the sensors, which sensors can be coordinated according to the principle of pattern recognition or with the aid of artificial neural net works to defined object gases.

In general, no particularly high reaction speed is called for especially for the application for evaluation of waste gases behind combustion plants and in connection with the determination of the effectiveness of catalysts in motor vehicles. Therefore, the selectivity relative to individual groups of gases, oxidizable or reducible, is increased if, in addition to the analysis of the impedance with the aid of different frequencies, also the temperature of the sensor element is changed. In case of higher temperatures, for example higher than about 350° C. in case of tin dioxide sensors, the sensitivity increases relative to oxidizable gases such as carbon monoxide or hydrocarbons and their fragments, and the sensitivity relative to nitrogen oxides, for example, decreases. Vice versa the sensitivity relative to nitrogen oxides, for example, is very high at low temperatures of, for example, 150° C., while the sensitivity relative to carbon monoxide, etc. decreases. This effect is substantially supported by the precedingly described methods. In addition to the selectivity, the stability of the arrangement increases, since no migration effects and no ion transport are to be observed any longer and also possibly included water molecules are no longer electrically dissociated at the high frequencies coordinated to the low temperatures, which is advantageous for the service live and the stability of the sensor elements.

Upon application for determining the combustion processes in combustion plants or upon application for the on-board diagnosis for determining the effectiveness of motor vehicle catalysts, sensor materials can be advantageously employed, where the sensor materials allow a higher operating temperature. Mixed oxides with a high content of tungsten dioxide, gallium oxide are advantageously proven. Vanadates and molybdates have also been tested as admixtures. In particular the low cross sensitivity relative to water is advantageously recited in connection with high operating temperatures and the recited sensitive materials.

It is common to all recited methods that the sensor-internal capacities and their influence on the impedance of the sensor are employed as a complex component for obtaining information under alternating currents having different frequencies.

Commercial Applicability

The invention method and the apparatus can be employed in particular for the quantitative and qualitative determination of gases, wherein the gases are oxidizable or reducible, in particular for the purpose of controlling ventilation plants in buildings and motor vehicles and for the purpose of monitoring combustion processes and waste gas catalyst plants. The usefulness of the invention comprises in particular that a statement relative to the presence and to the concentration of oxidizable gases can be made based on the change of the electrical path resistance of the sensor, and a statement relative to the presence and to the concentration of reducible gases with the aid of the electrical evaluation arrangement can be made based on the change of the electrical contact resistance.

It will be understood that each of the elements described above, or two or more together, may also find a useful application in other methods and types of devices for detecting gasses differing from the types described above.

While the invention has been illustrated and described as embodied in the context of a method and device for detecting oxidizable and/or reducible gasses in air, it is not intended to be limited to the details shown, since the various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A method for detecting oxidizable and/or reducible gases in the air for the purpose of controlling ventilation plants in buildings or motor vehicles and for the purpose of monitoring combustion processes or waste gas catalyst plants, comprising employing at least one electrically conductive and heated sensor (5.1; 7.2) furnished with contact electrodes (5.9; 5.10) and with a metallic sensor material;

employing an electric evaluation circuit;

passing an alternating current through the sensor (5.1; 7.2) wherein the alternating current either comprises at least two alternating currents of different frequency or is switched between at least two frequencies;

evaluating a changing of the capacities between the sensor material and the contact electrodes (5.9; 5.10) depending on a presence of reducible gases and on a presence of a standard gas by the evaluation circuit as an indicator on the one hand; and evaluating a changing of the capacities within the mass of the sensor material (sensitive material) depending on a presence of oxidizable gases and on a presence of a standard gas as an indicator on the other hand;

furnishing the sensor (5.1) as a component of an oscillating circuit (5.8; 7.1) for generating two different frequencies;

periodically changing the oscillation of the oscillating circuit by switching frequency-determining components between at least two frequencies;

individually evaluating and comparing the respective frequencies to the respective frequencies determined during operation of the sensor in standard air;

employing frequency deviations as a measure for the concentration of groups of gas present;

coordinating high frequencies always to reducible gases in the evaluation circuit and low frequencies always to oxidizable gases in the evaluation circuit; and determining the phase shifts, caused by the sensor-internal capacities, at individual frequencies; and decomposing the output signal into an imaginary part and into a real part, wherein the imaginary part and the real part represent a measure for the presence and kind of gases relative to values determined for standard air.

2. The method according to claim 1 comprising furnishing an alternating voltage with a generator (7.1) for different frequencies and feeding the alternating voltage to the sensor (7.2) through a phase shifter (7.3) and a rectangular wave modulator (7.4), and applying the output signal of the rectangular wave modulator (7.4) as well as the voltage, picked up over the sensor (7.2), to a mixer (7.5), averaging the output signal of the mixer (7.5) over a low pass filter (7.6), wherein the output voltage (7.7), obtained after the pass filter (7.6), represents a measure for the imaginary part or the real part or for a mixture of the two components of the sensor impedance depending on the setting of the phase shifter (7.3).

3. The method according to claim 1 further comprising switching the temperature of the sensor (5.1; 7.2) simultaneously with the switching of the frequencies, wherein the lower frequency is coordinated to the higher temperature, and wherein the higher frequency is coordinated to the lower temperature.

4. A method for detecting oxidizable and/or reducible gases in the air comprising employing a current-passing and heated sensor furnished with contact electrodes and with a metallic sensor material;

employing an oscillating circuit having frequency determining components for generating a first oscillation having a first frequency and a second oscillation having a second frequency;

connecting the sensor to the oscillating circuit for interacting with the first oscillation and with the second oscillation generated in the oscillating circuit;

switching the frequency-determining components between at the first oscillation and the second oscillation of the oscillating circuit;

changing periodically between the first oscillation and the second oscillation of the oscillating circuit;

passing a current associated with the first oscillation and, respectively, with the second oscillation through the sensor;

employing an electric evaluation circuit connected to the sensor;

monitoring a changing of the capacities between the sensor material and the contact electrodes depending on a presence of reducible gases and on a presence of a standard gas;

monitoring a changing of the capacities within a mass of the sensor material depending on a presence of oxidizable gases and on a presence of a standard gas;

evaluating changing values of capacities by an evaluation circuit as an indicator for a presence of a member of the group consisting of reducible gases, oxidizable gases and mixtures thereof.

5. The method for detecting oxidizable and/or reducible gases according to claim 4 further comprising individually evaluating respective frequencies and comparing the respective frequencies obtained by the evaluation to the respective frequencies determined during operation of the sensor in standard air;

employing frequency deviations as a measure for the concentration of groups of gas present, wherein the evaluation circuit coordinates high frequencies always to reducible gases and low frequencies always to oxidizable gases, and determines the phase shifts, caused by the sensor-internal capacities, at individual frequencies, and decomposes the output signal into an imaginary part and into a real part, wherein the imaginary part and the real part represent a measure for the presence and kind of gases relative to values determined for standard air.

6. A method for detecting oxidizable and/or reduceable gases in the air for the purpose of controlling of ventilation devices in buildings or motor vehicles and for the purpose of monitoring of a combustion process or in case of exhaust catalyst plants, comprising employing at least one sensor (5.1; 7.2) of metal oxide passed by a current and heatable and furnished with contact electrodes (5.9; 5.10) as well as under employment of an electrical evaluation circuit, passing an alternating current through the sensor (5.1; 7.2), wherein the alternating current comprises either at least two alternating currents of different frequencies or the alternating current is switched between at least two frequencies, and evaluating the change of the capacities between the sensor material and the contact electrodes by the evaluation circuit as a characteristic of the presence of reduceable gases and evaluating the change of the capacity within the mass of the sensor material (sensitive materials) as a characteristic of the presence of oxidizable gases, generating the different frequencies (fx,fy) with frequency determining device components, and with a switching circuit (5.8; 7.1), and wherein the sensor (5.1; 7.1) is a component of the oscillator circuit (5.8; 7.1) such that the oscillator circuit (5.8; 7.1), frequency determining components (5.2; 5.3) as well as the sensor (5.1; 7.1) form a changeable impedance, changing the oscillation of the oscillator circuit (5.8; 7.1) alternatingly by alternating switching of the frequency determining device components (5.2; 5.3) between at least the two frequencies (fx,fy) and wherein output signals of the oscillator circuit (5.8; 7.1) coordinated to these frequencies (fx,fy) are employed for calibration of a zero line in case the sensor (5.1; 7.1) is flushed with standard air, wherein always reduceable gases are coordinated to the higher frequency (fy) of the two frequencies (fx,fy) and wherein always oxidizable gases are coordinated to the lower frequency (fx) of the two frequencies (fx,fy), wherein the output signals of the oscillator circuit (5.8; 7.1) are changing relative to the zero line in case the sensor (5.1; 7.1) is flushed by gas deviating from standard air, wherein the higher frequency (fy) of the two frequencies (fx,fy) deviates from this higher frequency (fy) in case reduceable gases are present in the region of the sensor (5.1; 7.1) and the lower frequency (fx) of the two frequencies (fx,fy) deviates from this lower frequency (fx) if in contrast oxidizable gases are present in the region of the sensor (5.1; 7.1) and these respective deviations are evaluated.

7. A method for detecting oxidizable and/or reduceable gases in the air for the purpose of controlling of ventilation devices in buildings or motor vehicles and for the purpose of monitoring of a combustion process or in case of exhaust catalyst plants, by employing of at least one sensor (5.1; 7.2) of metal oxide flown through by a current and heatable and furnished with contact electrodes (5.9; 5.10) as well as under employment of an electrical evaluation circuit, wherein the sensor (5.1; 7.2) is flown through by an alternating current, wherein the alternating current comprises either at least two alternating currents of different frequencies or the alternating current is switched between at least two frequencies, and on the one hand the change of the capacities between the sensor material and the contact electrodes is evaluated by the evaluation circuit as a characteristic of the presence of reduceable gases and on the other hand the change of the capacity within the mass of the sensor material (sensitive materials) is evaluated as a characteristic of the presence of oxidizable gases, wherein the different frequencies (fx,fy) are generated with frequency determining device components such as capacitors (5.2; 5.3), and with a switching circuit (5.8; 7.1), and wherein the sensor (5.1; 7.1) is a component of the oscillator circuit (5.8; 7.1) such that the oscillator circuit (5.8; 7.1), frequency determining components (5.2; 5.3) as well as the sensor (5.1; 7.1) form a changeable impedance, wherein the oscillation of the oscillator circuit (5.8; 7.1) is changed alternatingly by alternating switching of the frequency determining device components (5.2; 5.3) between at least the two frequencies (fx,fy) and wherein output signals of the oscillator circuit (5.8; 7.1) coordinated to these frequencies (fx,fy) are employed for calibration of a zero line in case the sensor (5.1; 7.1) is flushed with standard air, wherein always reduceable gases are coordinated to the higher frequency (fy) of the two frequencies (fx,fy) and wherein always oxidizable gases are coordinated to the lower frequency (fx) of the two frequencies (fx,fy), wherein the output signals of the oscillator circuit (5.8; 7.1) are changing relative to the zero line in case the sensor (5.1; 7.1) is flushed by gas deviating from standard air, wherein in case of a deviation the higher frequency (fy) of the two frequencies (fx,fy) from this higher frequency (fy) the presence of reduceable gases is detected in the region of the sensor (5.1; 7.1) and wherein in case of a deviation of the lower frequency (fx) of the two frequencies (fx,fy) from this lower frequency (fx) the presence of oxidizable gases is detected in the region of the sensor (5.1; 7.1).

8. The method according to claim 7 further comprising individually evaluating the respective frequencies and wherein the starting signal is decomposed into an imaginary part and into a real part and that the values determined for standard air represent a measure for a presence and for a kind of a gas.

9. The method according to claim 8, further comprising feeding an alternating voltage furnished by a generator (7.1) for different frequencies to the sensor (7.2) through a phase shifter (7.3) and a rectangular wave modulator (7.4), and applying the output signal of the rectangular wave modulator (7.4) as well as the voltage, picked up over the sensor (7.2), to a mixer (7.5), averaging the output signal of the mixer (7.5) over a low pass filter (7.6), wherein the output voltage (7.7), obtained after the pass filter (7.6), represents a measure for the imaginary part or the real part or for a mixture of the two components of the sensor impedance depending on the setting of the phase shifter (7.3).

10. The method according to claim 7, further comprising switching the temperature of the sensor (5.1; 7.2) simultaneously with the switching of the frequencies, wherein the lower frequency is coordinated to the higher temperature, and wherein the higher frequency is coordinated to the lower temperature.

11. The method according to claim 7, further comprising disposing the heated sensor (5.1) with its contact electrodes in parallel to the oscillator circuit (5.8), putting the output signal of the oscillator circuit (5.8) onto the microprocessor (uP, 5.5), connecting two capacitors (5.2, 5.3) in series to serve the frequency determining device component, wherein the second capacitor (5.2) is connected to the input (5.9) of the oscillator circuit (5.8, 7.1) and wherein the second capacitor (5.2) works on the input (5.9) of the oscillator circuit (5.8, 7.1) and wherein the first capacitor (5.3) is shorted alternatingly or periodically for changing the input capacitance of the oscillator circuit (5.8).

12. The method according to claim 11, further comprising performing the alternating shorting of the first capacitor (5.3) with a field effect transistor (5.4) in connection with the microprocessor (5.5, uP), disposing the drain connection and the source connection (5.6) of the field effect transistor (5.4) in the microprocessor (5.5, uP) in the middle between the two capacitors (5.2) and (5.3), connecting the first capacitor (5.3) to ground, wherein the gate connection (5.7) of the field effect transistor (5.4) is connected to the microprocessor (5.5, uP), and wherein the field effect transistor (5.4) is controlled by the microprocessor (5.5, up).

13. The method according to claim 12 further comprising constructing the circuit for a frequency of about 3 to 5 khz of the oscillator circuit (5.8) to be established in case of a sensor (5.1) adapted to standard air upon a short circuiting of the first capacitor (5.3), whereas in contrast a frequency of about 150 khz of the oscillator circuit (5.8) establishes upon a series connection of the two capacitors (5.3, 5.2), wherein the input capacity of the oscillator circuit (5.8) is changed correspondingly by a continuous switching of the field effect transistor (5.4) between a short circuit of the first capacitor (5.3) and a series connection of the two capacitors (5.3, 5.2), whereby the output frequency of the oscillator circuit (5.8) is changed.

14. An apparatus for detecting oxidizable gases and/or reducible gases in the air for the purpose of controlling ventilation plants in buildings or vehicles and for the purpose of monitoring combustion processes or waste gas catalyst plants, comprising at least one electrically conductive and heated sensor (5.1; 7.2) furnished with contact electrodes (5.9; 5.10) and with a metallic sensor material, wherein the sensor (5.1; 7.2) is passed through by an alternating current, the sensor (5.1) is a component of an oscillating circuit (5.8; 7.1) for generating two different frequencies, wherein the oscillation of the oscillating circuit is periodically changeable by switching frequency-determining components between at least two frequencies, wherein the respective frequencies are individually evaluated and are compared with respective frequencies, determined during operation of the sensor in standard air, and wherein frequency deviations are employed as a measure for the concentration of groups of gases present;

an electric evaluation circuit, wherein the alternating current either consists of at least two alternating currents having different frequencies or is switchable between at least two frequencies, and wherein the change of the capacities between the sensor material and the contact electrodes (5.9; 5.10) is evaluated by the evaluation circuit as an indicator of the presence of reducible gases and wherein the change of the capacities within the mass of the sensor material (sensitive material) is evaluated as an indicator of the presence of oxidizable gases, wherein the evaluation circuit coordinates high frequencies always to reducible gases and low frequencies always to oxidizable gases, and determines the phase shifts, caused by the sensor-internal capacities, at the individual frequencies, and decomposes the output signal into an imaginary part and into a real part, which imaginary part and which real part represent a measure for the presence and type of gases relative to values determined under standard air.

15. The apparatus according to claim 14 further comprising a phase shifter (7.3), a rectangular wave modulator (7.4), a generator (7.1) furnishing an alternating voltage for different frequencies is fed to the sensor (7.2) through the phase shifter (7.3) and the rectangular wave modulator (7.4), and a mixer (7.5), wherein the output signal of the rectangular wave modulator (7.4) as well as the voltage, picked up over the sensor (7.2), are applied to the mixer (7.5), a low pass filter (7.6), wherein the output signal of the mixer (7.5) is averaged over the low pass filter (7.6), wherein the output voltage (7.7), obtained after the low pass filter (7.6), represents a measure for the imaginary part or the real part or for a mixture of the two components of the sensor impedance depending on the setting of the phase shifter (7.3).

16. A device for detecting oxidizable and/or reduceable gases in the air for the purpose of controlling of air ventilation devices in buildings or motor vehicles and for the purpose of monitoring the combustion processes or of waste gas catalyst plants, comprising at least one sensor (5.1; 7.2) made of metal oxide, passed by an electrical current, heatable and furnished with contact electrodes (5.9; 5.10);

an electrical evaluation circuit connected to the sensor, wherein the sensor (5.1; 7.2) is flown through by an alternating current, wherein the alternating current comprises either at least two alternating currents of different frequency or is switchable between at least two frequencies for evaluation on the one hand of the change of the capacities between the sensor material and the contact electrodes (5.9; 5.10) by the evaluation circuit as a characteristic of the presence of reduceable gases and on the other hand the change of the capacities within the mass of the sensor material (sensitive material) as a characteristic of the presence of oxidizable gases, wherein frequency determining device components such as capacitors (5.2; 5.3), and an oscillator circuit (5.8; 7.1), which together generate the most different frequencies (fx,fy), wherein the sensor (5.1; 7.1) is a component of the oscillator circuit (5.8; 7.1) such that the oscillating circuit (5.8; 7.1), frequency determining device components (5.2; 5.3) as well as sensor (5.1; 7.1) from a changeable impedance, wherein the oscillation of the oscillator circuit (5.8; 7.1) is alternatingly changeable between at least the two frequencies (fx,fy) by alternating switching of the frequency determining device components (5.2; 5.3) and wherein the output signals of the oscillator circuit (5.8; 7.1) coordinated to these frequencies (fx,fy) are employed for calibration of a zero line in case the sensor (5.1; 7.1) is flushed with standard air, wherein always reduceable gases are coordinated to the higher frequency (fy) of the two frequencies (fx,fy) and wherein always oxidizable gases are coordinated to the lower frequency (fx) of the two frequencies (fx,fy), wherein the output signals of the oscillator circuit (5.8; 7.1) change relative to the zero line in case the sensor (5.1; 7.1) is flushed by gas deviating from standard air, wherein in case of a deviation the higher frequency (fy) of the two frequencies (fx,fy) from this higher frequency (fy) the presence of reduceable gases is detected in the region of the sensor (5.1; 7.1) and wherein in case of a deviation of the lower frequency (fx) of the two frequencies (fx,fy) from this lower frequency (fx) the presence of oxidizable gases is detected in the region of the sensor (5.1; 7.1).

17. The device according to claims 16 further comprising a phase shifter (7.3), a rectangular wave modulator (7.4), a generator (7.1) for feeding an alternating voltage furnished by a generator (7.1) for different frequencies to the sensor (7.2) through the phase shifter (7.3) and the rectangular wave modulator (7.4), and a mixer (7.5), wherein the output signal of the rectangular wave modulator (7.4) as well as the voltage, picked up over the sensor (7.2), are applied to the mixer (7.5), wherein the output signal of the mixer (7.5) is averaged over a low pass filter (7.6), wherein the output voltage (7.7), obtained after the pass filter (7.6), represents a measure for the imaginary part or the real part or for a mixture of the two components of the sensor impedance depending on the setting of the phase shifter (7.3).

18. The device according to claim 16, wherein the temperature of the sensor (5.1; 7.2) is switchable and occurs simultaneously with the sitching of the frequencies, wherein the lower frequency is coordinated to the higher temperature, and wherein the higher frequency is coordinated to the lower temperature.

19. The device according to claim 16, wherein the heated sensor (5.1) is switched with its contact electrodes (5.9; 5.10) parallel to the oscillating circuit (5.8), wherein the output signal of the oscillating circuit (5.8) is applied to the microprocessor (çP) (5.5), wherein a series connection of two capacitors (5.2; 5.3) is arranged at an input of the oscillating circuit (5.8), wherein one capacitor (5.3) of the series connection is alternatingly short-circuitable for changing the input capacitance of the oscillating circuit (5.8).

20. The device according to claim 19, wherein the internal counter of the microprocessor (5.5, uP) determines the frequency delivered by the oscillator circuit (5.8).

21. The device according to claim 16, further comprising an oscillator circuit (5.8), a heatable sensor (5.1) forming part of the oscillator circuit (5.8), wherein the heatable sensor (5.1) with its contact electrodes is disposed in parallel to the oscillator circuit (5.8), wherein the output signal of the oscillator circuit (5.8) is put onto the microprocessor (uP, 5.5), wherein a first capacitor (5.3) connected in series with a second capacitor (5.2) which second capacitor (5.2) is connected to the input (5.9) of the oscillator circuit (5.8) and to a contact electrode (5.9) of the heatable sensor (5.1) and wherein the first capacitor (5.3) is shorted alternatingly or periodically.

22. The device according to claim 21, further comprising a field effect transistor (5.4), wherein the alternating shorting of the first capacitor (5.3) is performed by the field effect transistor (5.4) in connection with the microprocessor (5.5, uP), wherein the drain connection and the source connection (5.6) of the field effect transistor (5.4) is disposed in the microprocessor (5.5, uP) in the middle between the two capacitors (5.2) and (5.3), wherein the first capacitor (5.3) is connected to ground, wherein the gate connection (5.7) of the field effect transistor (5.4) is connected to the microprocessor (5.5, uP), and wherein the field effect transistor (5.4) is controlled by the microprocessor (5.5, uP).

23. The device according to claim 22, wherein the circuit is constructed such that a frequency of about 3 to 5 khz of the oscillator circuit (5.8) establishes in case of a sensor (5.1) adapted to standard air upon a short circuiting of the first capacitor (5.3), whereas in contrast a frequency of about 150 khz of the oscillator circuit (5.8) establishes upon a series connection of the two capacitors (5.3, 5.2), wherein the input capacity of the oscillator circuit (5.8) is changed correspondingly by a continuous switching of the field effect transistor (5.4) between a short circuit of the first capacitor (5.3) and a series connection of the two capacitors (5.3, 5.2), whereby the output frequency of the oscillator circuit (5.8) is changed.

24. A device for detecting oxidizable and/or reduceable gases in the air for the purpose of controlling of air ventilation devices in buildings or motor vehicles and for the purpose of monitoring the combustion processes or of waste gas catalyst plants, comprising at least one sensor (5.1; 7.2) made of metal oxide, passed by an electrical current, heatable and furnished with contact electrodes (5.9; 5.10), an electrical evaluation circuit connected to the sensor, wherein the sensor (5.1; 7.2) is passed by an alternating current, wherein the alternating current comprises either at least two alternating currents of different frequency or is switchable between at least two frequencies for evaluation on the one hand of the change of the capacities between the sensor material and the contact electrodes (5.9; 5.10) by the evaluation circuit as a characteristic of the presence of reduceable gases and on the other hand the change of the capacities within the mass of the sensor material (sensitive material) as a characteristic of the presence of oxidizable gases, wherein frequency determining device components such as capacitors (5.2; 5.3), and an oscillator circuit (5.8; 7.1), which together generate the most different frequencies (fx,fy), wherein the sensor (5.1; 7.1) is a component of the oscillator circuit (5.8; 7.1) such that the oscillating circuit (5.8; 7.1), frequency determining device components (5.2; 5.3) as well as sensor (5.1; 7.1) from a changeable impedance, wherein the oscillation of the oscillator circuit (5.8; 7.1) is alternatingly changeable between at least the two frequencies (fx,fy) by alternating switching of the frequency determining device components (5.2; 5.3) and wherein the output signals of the oscillator circuit (5.8; 7.1) coordinated to these frequencies (fx,fy) are employed for calibration of a zero line in case the sensor (5.1; 7.1) is flushed with standard air, wherein always reduceable gases are coordinated to the higher frequency (fy) of the two frequencies (fx,fy) and wherein always oxidizable gases are coordinated to the lower frequency (fx) of the two frequencies (fx,fy), wherein the output signals of the oscillator circuit (5.8; 7.1) change relative to the zero line in case the sensor (5.1; 7.1) is flushed by gas deviating from standard air, wherein a deviation of the higher frequency (fy) of the two frequencies (fx,fy) is present in case reduceable gases are present in the region of the sensor (5.1; 7.1) and wherein a deviation of the lower frequency (fx) of the two frequencies (fx,fy) of this lower frequency (fx) is present if in contrast oxidizable gases are present in the region of the sensor (5.1; 7.1) and wherein the respective deviations are evaluated.

* * * * *